(12) United States Patent
Kruecker

(10) Patent No.: US 8,364,245 B2
(45) Date of Patent: Jan. 29, 2013

(54) COORDINATE SYSTEM REGISTRATION

(75) Inventor: Jochen Kruecker, Washington, DC (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 790 days.

(21) Appl. No.: 12/301,238

(22) PCT Filed: May 11, 2007

(86) PCT No.: PCT/IB2007/051800
§ 371 (c)(1),
(2), (4) Date: Nov. 18, 2008

(87) PCT Pub. No.: WO2007/135609
PCT Pub. Date: Nov. 29, 2007

(65) Prior Publication Data
US 2009/0292201 A1    Nov. 26, 2009

Related U.S. Application Data

(60) Provisional application No. 60/802,936, filed on May 24, 2006, provisional application No. 60/870,924, filed on Dec. 20, 2006.

(51) Int. Cl.
*A61B 5/05* (2006.01)
(52) U.S. Cl. ........ 600/426; 600/407; 600/423; 600/424; 600/427; 600/433; 382/128; 382/132; 382/154; 382/294
(58) Field of Classification Search .................. 600/407, 600/423, 424, 427, 433, 426; 382/154, 128, 382/132, 294
See application file for complete search history.

(56) References Cited

U.S. PATENT DOCUMENTS

| | | | | |
|---|---|---|---|---|
| 7,646,899 | B2 * | 1/2010 | Fitzpatrick | 382/128 |
| 7,831,086 | B2 * | 11/2010 | Kondo et al. | 382/154 |
| 2003/0231793 | A1 * | 12/2003 | Crampton | 382/154 |
| 2004/0171924 | A1 * | 9/2004 | Mire et al. | 600/407 |
| 2005/0012745 | A1 * | 1/2005 | Kondo et al. | 345/427 |
| 2006/0036167 | A1 * | 2/2006 | Shina | 600/433 |
| 2006/0147100 | A1 * | 7/2006 | Fitzpatrick | 382/131 |
| 2007/0135803 | A1 * | 6/2007 | Belson | 606/1 |
| 2007/0270685 | A1 * | 11/2007 | Kang et al. | 600/424 |
| 2008/0010705 | A1 * | 1/2008 | Quaid et al. | 901/8 |
| 2008/0010706 | A1 * | 1/2008 | Moses et al. | 901/8 |
| 2009/0234217 | A1 * | 9/2009 | Mire et al. | 600/407 |
| 2010/0210938 | A1 * | 8/2010 | Verard et al. | 600/424 |

FOREIGN PATENT DOCUMENTS
EP    0908146 A2    4/1999

OTHER PUBLICATIONS

F. Banovac et al., "Precision Targeting of Liver Lesions Using a Novel Electromagnetic Navigation Device in Physiologic Phantom and Swine", Med. Phys. 32(8), Aug. 2005, pp. 2698-2705.
J. Kruecker et al., "Clinical Evaluation of Electromagnetic Tracking for Biopsy and Radiofrequency Ablation Guidance", Philips Research North America, Briarcliff Manor, NY, USA, pp. 169-172.
H. Zhang et al., "Two-Stage Registration for Real-Time Deformable Compensation Using an Electromagnetic Tracking Device", Image Science & Information System Center, Dept. of Radiology, Georgetown University, Washington, DC, USA, Springer-Verlag Berlin Heidelberg 2005, pp. 992-999.

* cited by examiner

Primary Examiner — Tse Chen
Assistant Examiner — Baisakhi Roy

(57) ABSTRACT

A system includes a component that updates a registration between an image space coordinate system and an interventional space coordinate system. The registration update is based on interventional device position information within a patient obtained from intermediate image data indicative of the interventional device location and a position sensor that is located on an interventional device within the patient.

27 Claims, 3 Drawing Sheets

COORDINATE SYSTEM REGISTRATION

CROSS REFERENCE TO RELATED CASES

Applicant claims the benefit of International Application Number PCT/IB2007/051800, filed May 11, 2007, and Provisional Application Ser. Nos. 60/870,924, filed Dec. 20, 2006 and 60/802,936, filed May 24, 2006.

The present application generally relates to registering physical and image space coordinate systems. While it finds particular application to interventional radiology, it also relates to other medical and non-medical imaging applications.

Interventional medical procedures such as minimally invasive surgery including radiofrequency ablation call for substantially reliable and precise navigation along predefined paths to predetermined target locations or destinations since the interventional device cannot be seen once it is inserted beneath the skin. To facilitate locating the target within the patient and determining a suitable path to the target for the interventional device, many interventional procedures are planned using a pre-procedure image(s) from a modality such as x-ray, computed tomography (CT), ultrasound (US), or magnetic resonance imaging (MRI). Such an image allows the clinician to non-invasively see the target within the patient.

Traditionally, the clinician visually relates the anatomy within a patient from the pre-procedural image to the non-visible anatomy within the patient to determine the location of the target and a suitable path from the skin to the target. However, this technique does not provide for reliable and precise navigation of an interventional device such as a needle, a catheter, or a guide wire within the patient to the target. One reason for this is that the spatial relationship between the anatomy shown in the image and the anatomy within the patient is unknown to the interventionist.

The position accuracy of this approach may be improved by observing the position of the interventional device as it is incrementally advanced along a planned path within the patient. In one instance, this is achieved by scanning the patient after each incremental advance of the interventional device and generating an intermediate image indicative of the positional state of the interventional device. Unfortunately, the spatial relationship between the anatomy in the image and the actual patient anatomy is still unknown. As a result, the position accuracy of the interventional device is still less than desired.

In order to improve the position accuracy, a coordinate system of the pre-procedural image is registered to a coordinate system of the interventional device. This defines a relationship between the anatomy in the image and the anatomy in the patient. This relationship allows a feature in one of the coordinate systems to be spatially mapped to the other coordinate system. One suitable registration technique includes attaching fiducial markers to the patient and using the markers to correlate the coordinate systems. For the image space coordinate system, the markers are attached to the patient before scanning. The markers are then localized in the resulting image data. For the interventional space coordinate system, coordinates of the markers are spatially identified on the patient with a positional tracking device. A transformation between the image and interventional space coordinate systems is then generated.

Assuming a fixed spatial relationship between the patient and the interventional system, a path to the target for the interventional device is planned using the pre-procedure image. In instances in which the markers are placed on the skin, the distance between the reference points (the markers) and target may lead to positional inaccuracies. Placing the markers under the skin requires an invasive step. Another shortcoming with this technique is that the coordinate system registration may be compromised by patient motion.

In another approach, an interventional device tracking sensor is used in conjunction with the pre-procedural image to verify the position of the interventional device as it is maneuvered within the patient. With this approach, the tracking sensor is attached to a portion of the interventional device that is inserted into the patient and the position of the sensor is read by an electromagnetic, magnetic, optical, ultrasonic, or other position measurement device. The clinician advances the interventional device along the planned path using the interventional device position measurement as a guide. Unfortunately, the positional accuracy of the interventional device may be compromised due to the measurement inaccuracies inherent in the position measurement device and electromagnetic, magnetic, acoustic, or other interference between the device and the environment.

Aspects of the present application address the above-referenced matters and others.

According to one aspect, a system includes a component that updates a registration between an image space coordinate system and an interventional space coordinate system based on interventional device position information within a patient obtained from intermediate image data indicative of the interventional device location and a position sensor that is located on an interventional device and within the patient.

According to another aspect, a system includes a first component that registers an image space coordinate system and an interventional space coordinate system based on the spatial location of at least three fiducial markers identified within corresponding image data and the spatial coordinates of the at least three fiducial markers spatially identified on a patient with a position measurement device. The system further includes a second component that uses interventional device position information obtained from an intermediate image generated from image data acquired after the interventional device is advanced into the patient to update a position measurement performed by the position measurement device.

In another aspect, a method includes registering an image space coordinate system with an interventional system coordinate system based on fiducial marker position information for a plurality of fiducial markers. The method further includes updating the registration based on interventional device position information obtained from an intermediate image, interventional device position information obtained from a position tracking sensor located on the interventional device, and the spatial location of the at least three fiducial markers to update the registration. The interventional device position information is obtained from the intermediate image and the position tracking sensor after advancing the interventional device along a path within the patient.

In yet another aspect, a system/component includes a computer readable storage medium containing instructions which, when executed by a computer, cause the computer to carry out the steps of: registering an image space coordinate system with an interventional system coordinate system based on fiducial marker position information for a plurality of fiducial markers and updating the registration based on interventional device position information obtained from an intermediate image, interventional device position information obtained from a position tracking sensor located near the tip of the interventional device, and the spatial location of the at least three fiducial markers to update the registration. The interventional device position information is obtained from the intermediate image and the position tracking sensor after advancing the interventional device along a planned path within the patient.

In still another aspect, a system includes a means for registering an image space coordinate system with an interventional system coordinate system based on fiducial marker position information for a plurality of fiducial markers and a means for updating the registration based on interventional device position information obtained from an intermediate image and interventional device position information obtained from a position tracking sensor on the interventional device and the spatial location of the plurality of fiducial markers.

Still further aspects of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
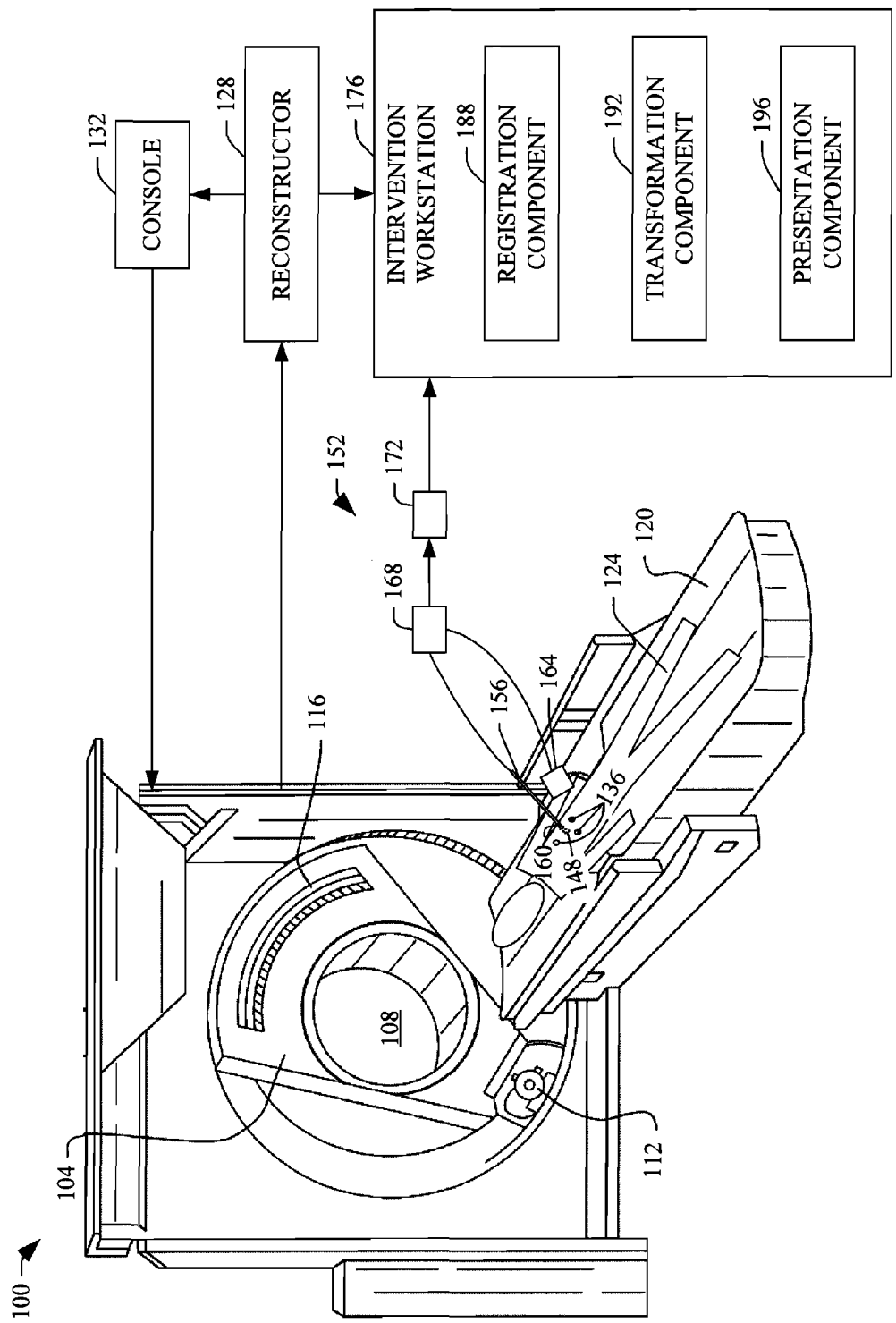
FIG. 1 illustrates an exemplary imaging system.

With reference to FIG. 1, a computed tomography (CT) scanner 100 includes a rotating gantry portion 104 which rotates about an examination region 108 around a longitudinal or z-axis.

An x-ray source 112 such as an x-ray tube is suspended to and rotates with the rotating gantry portion 104. The x-ray source 112 generates and emits radiation that traverses the examination region 108 and objects disposed therein.

The rotating gantry portion 104 also supports an x-ray detector 116, which is located opposite the x-ray source 112 with respect to the examination region 108. The x-ray detector 116 includes a generally two-dimensional array of detector elements that detects radiation that traverses the examination region 108.

The x-ray detector 116 rotates with the rotating gantry portion 104 in coordination with the x-ray source 112 about the examination region 108 so that x-ray projections from the x-ray source 112 are acquired from a plurality of different angular positions during data acquisition. The angular extent of the data acquisition is such that x-ray projections are obtained over at least one hundred and eighty (180) degrees plus a fan angle. The x-ray detector 116 generates projection data indicative of the detected radiation.

An object support 120 such as a couch supports an object such as patient 124 in the examination region 108. The object support 120 is movable so as to guide the patient 124 with respect to the examination region 108 for an imaging procedure.

A reconstructor 128 reconstructs the projection data from the x-ray detector 116 to generate volumetric image data indicative of the examination region 108 and the portion of the patient 124 therein. One or more images are generated from the volumetric image data.

A general purpose computer serves as an operator console 132. The console 132 includes for example a human readable output device such as a monitor or display and an input device such as a keyboard and mouse. Software resident on the console 132 allows the operator to control and interact with the scanner 100, for example, through a graphical user interface (GUI).

In the illustrated embodiment, a plurality of fiducial markers such as three fiducial markers 136 are advantageously placed on a portion of the patient 124 that is scanned. The markers 136 are positioned in a generally non-collinear orientation on the skin of the patient with respect to a region of interest 148 within the patient 124 so as to provide references within a coordinate system.

The markers 136 include a material(s) with an attenuation coefficient that renders them distinguishable from biological tissue in the volumetric image data or the one or more images. The markers 136 are located or identified in the volumetric image data or images using known techniques. For instance, one technique may differentiate between the markers 136 and biological tissue using Hounsfield units or CT numbers.

An interventional system 152 is used in connection with the scanner 100 to perform interventional procedures.

The interventional system 152 includes a probe 156 and a field generator 164. The probe 156, which is an interventional device such as a needle, a catheter or a guide wire for example, is inserted into the patient 124 and is suitably positioned with respect to the region of interest 148 (or some other destination or target) for performing the interventional procedure.

A sensor 160 is coupled to the probe 156 and provides positional feedback or information about the probe 156. The sensor 160 includes an electromagnetic coil or marker that senses an induced electromagnetic field generated by the field generator 164 and generates a corresponding positional signal.

In the illustrated embodiment, the sensor 160 is advantageously positioned near a distal end of the probe 156 that is inserted into the patient so as to provide positional information about a location substantially close to the end of the probe 156 in the patient. Such positioning also allows the sensor 160 to track bending or other distortions of the end of the probe 156.

A position measurement component 168 generates position information about the probe 156 from a signal from the sensor 160. For example, the component 168 uses the signal of the sensor to determine the position of the probe 156 in three dimensional space. The position information is used to guide the probe 156 as it is inserted and maneuvered beneath the skin with respect to the region of interest 148.

A control component 172 controls the field generator 164, the sensor 160, and the positional measurement component 168.

An interventional workstation 176 includes a registration component 188 that correlates the image and the interventional space coordinate systems. From the image data, fiducial marker spatial information or coordinates are obtained using known techniques. For example, in one implementation imaging processing software allows a user to manually, semi-automatically or automatically spatially identify the non-collinearly placed fiducial markers 136 within the image data.

For the interventional space coordinate system, fiducial marker position information is obtained from the position measurement device 168. For example, in one implementation the relative spatial orientation of the markers 136 is obtained by inducing an electromagnetic field about the markers 136 and identifying each marker by touching the marker with the probe 156 or other position pointer device. From this information, the registration component 188 correlates the interventional space coordinate system to the image space coordinate system.

A transformation component 192 generates a transformation between the coordinate systems. The transformation component 192 is configurable to generate a rigid, elastic, or affine transformation, depending to the particular application. The transformation is used to map coordinates between coordinate system so that an object in one of the coordinate systems can be located in the other coordinate system by mapping coordinates.

A presentation component 196 presents the image data and the sensor positional data. This data is used to guide an interventionist while performing an interventional procedure.

In the illustrated embodiment, intermediate scans are performed to acquire image data and/or images indicative of the position of the probe 156 at incremental advances as it is moved along the path to the target. Before, during or after these scans, probe positional measurements are read from the sensor 160. A combination of the intermediate image data and the corresponding positional data is used to update the registration and adjust for positional measurement inaccuracies due to the inaccuracies of the positional measurement device 168 and interference from the environment as described in greater detail below.

Figure 2:
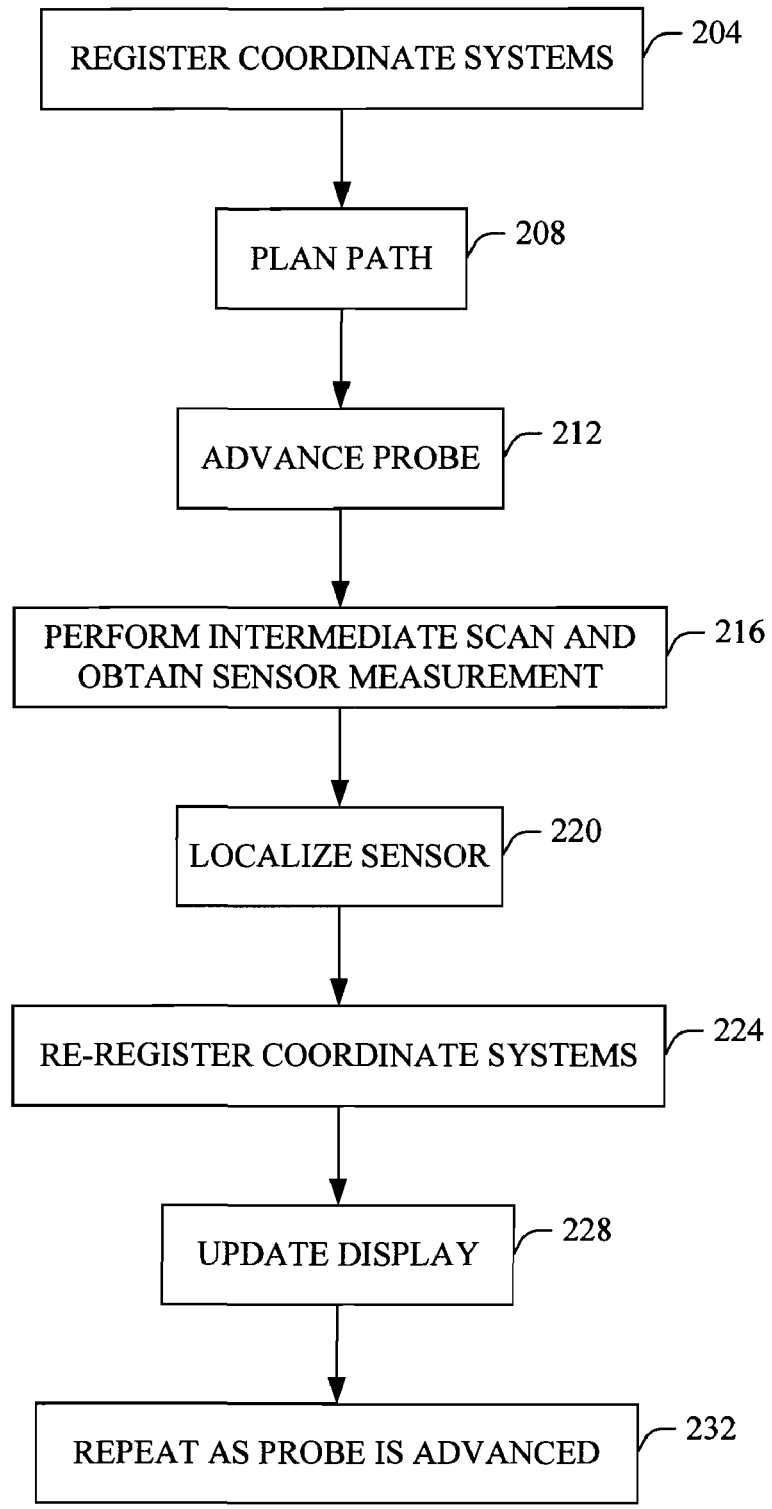
FIG. 2 illustrates a first exemplary method.

FIG. 2 describes an exemplary method for updating the registration between coordinate systems.

At 204, image and interventional space coordinate systems are registered.

At 208, a pre-procedural image and the registration of the coordinate systems are used to plan a path for the probe 156 in interventional space from the skin to the target using known planning techniques.

At 212, the probe 156 is advanced along the path to a first position using the sensor positional feedback displayed by the presentation component 192 as a guide.

At 216, an intermediate scan is performed by the scanner 100 and a sensor position reading is acquired by the interventional system 152. As noted above, the position reading can be obtained before, during or after the scan. In general, the position reading is performed at about the same time as the scan so that the image data and the position data are substantially reflective of the same motion state.

At 220, the sensor 160 is localized within the intermediate image data.

At 224, the coordinate systems are re-registered using the fiducial marker coordinates obtained from the pre-procedural image and the coordinates of the sensor 160 from the intermediate image data and the original and newly acquired marker and sensor positional information obtained from the sensor 160. As a result, the re-computed registration is based on four data points instead of three like the initial registration.

At 228, the presentation component 192 displays the updated position data and one or both of the images.

At 232, the steps 212-228 are repeated as the probe 156 is advanced.

In general, a subsequent registration improves the registration between the coordinate systems. In one instance, the improvement is due to additional data points. In another instance, the improvement is a consequence of using data points that are relatively closer to the target, which may decrease the error caused by the distance between the reference markers and the target. In yet another instance, the improvement is a result of acquiring data points more reflective of the current motion state since the later positional measurements are obtained later in time.

Figure 3:
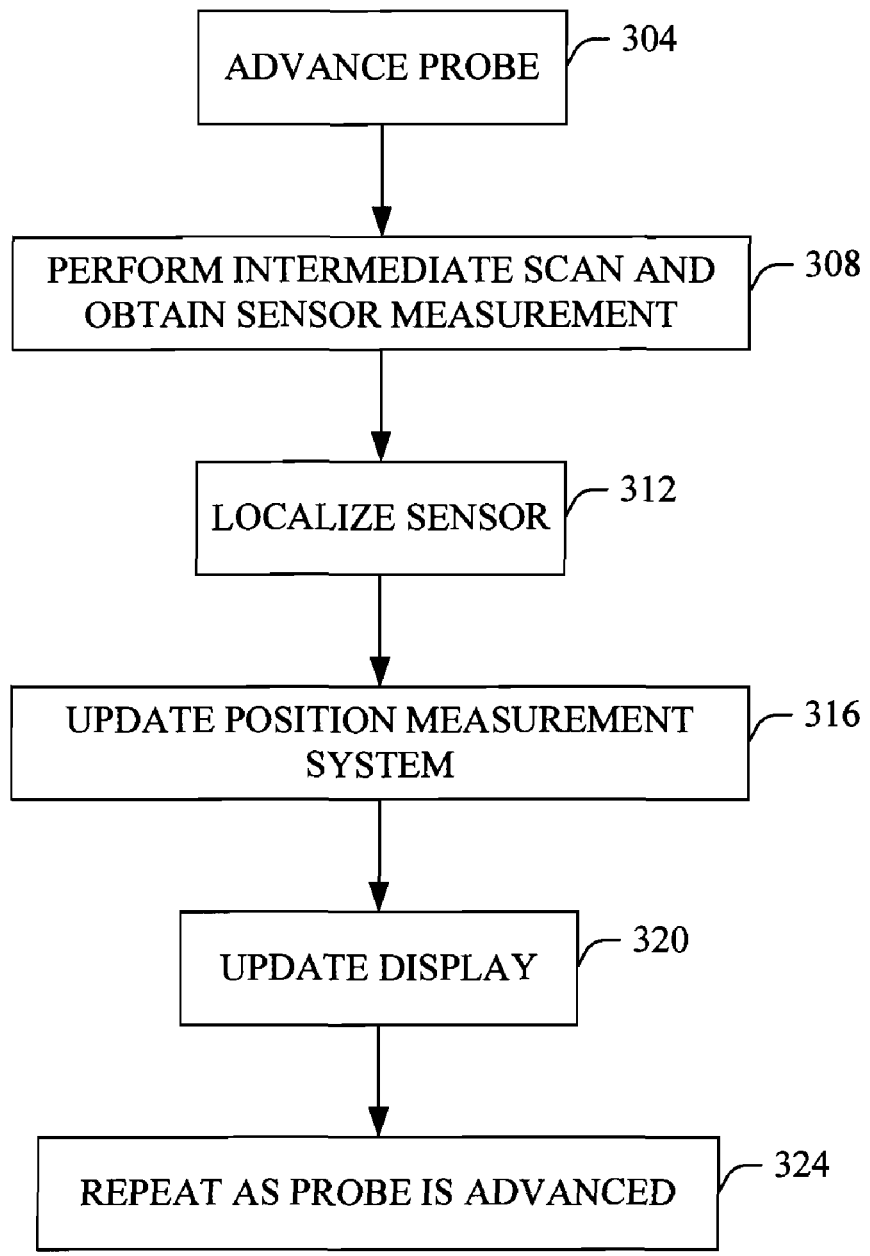
FIG. 3 illustrates a second exemplary method.

FIG. 3 describes an exemplary method for adjusting the system for position inaccuracies. For this example, assume that the intervention system and image space coordinate systems are registered as described above and that the positional state of the anatomy at the time of the intermediate scan is substantially the same as the positional state at the time of the pre-procedure scan.

At 304, the probe 156 is advanced to a first position along a path within the subject.

At 308, an intermediate scan of the sensor 160 and a position reading of the sensor 160 reading are respectively acquired via the scanner 100 and the system 152.

At 312, the sensor 160 is localized within the intermediate image.

At 316, the position information obtained from the intermediate image is used to adjust or re-calibrate the position measurement device 168 so that its position measurement reflects the actual position of the sensor 160. It is noted that the position information obtained from the intermediate image substantially represents the actual position of the sensor 160, whereas sensor position information obtained from the position measurement device 168 includes inaccuracies due to the measurement limitations of the device 168 and interference with ferromagnetic components of the scanner 100.

At 320, the presentation component 192 displays the updated position data and the images.

At 324, the steps 304-320 are repeated to adjust the position readout of the position measurement device 168 after each advance of the probe 156 along the interventional path.

Incrementally moving the probe 156 along the path and updating the calibration of the positional measurement device continues until the probe 160 is positioned at a desired location along the path. Periodically adjusting for position measurement system in accuracies improves navigation of the probe 156 to the target relative to a configuration in which the inaccuracies are not addressed.

Other aspects are described below.

In the illustrated example, each subsequent registration uses the newly acquired sensor position data from the image data and position measurement device 168 and the previously acquired fiducial marker position data. In an alternative implementation, updated fiducial marker position data is also acquired with each advance of the probe 156, and the newly acquired sensor and fiducial marker position data are used to update the registration. One advantage of this approach is that it mitigates motion distortion that changes the spatial relationship between the markers 136. A different probe or tracking device is used to identify the marker coordinates in interventional space since the probe 156 is inserted within the patient.

It is to be appreciated that for each subsequent registration, one or more including all of the previously acquired sensor position measurements are used to register the coordinate systems. In another alternative, the position measurements are weighted so that position measurements acquired later in time, which are more likely to represent the current motion state, contribute to the registration to a greater extent.

The new registration may be used to display the sensor 160 relative to the pre-procedure or intermediate image.

In another embodiment, the console 132 and the workstation 176 are the same system.

The registration component 184 and the transformation component 188 may be implemented by way of computer readable instructions which, when executed by a computer processor(s), cause the processor(s) to carry out the described techniques. In such a case, the instructions are stored in a computer readable storage medium associated with or otherwise accessible to the relevant computer.

In the illustrated embodiment, a CT scanner is used to acquire the data for the pre-procedural and intermediate images. Additionally or alternatively, magnetic resonance imaging (MRI), Ultrasound (US), three-dimensional (3D) x-ray, or other techniques can be used to acquire the data for the pre-procedural and/or intermediate images.

Also, in the illustrated embodiment, the position measurement device is based on an electromagnetic technique. Additionally or alternatively, position measurement devices using magnetic, optical, ultrasonic, or other techniques for spatial tracking may be used. In this case, the electromagnetic field generator 164 is replaced by an optical, magnetic, ultrasonic or other source or generator.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An interventional system that employs medical imaging data as a guide for advancing an interventional device, comprising:
   a registration component that performs a first registration between an image space coordinate system and an interventional space coordinate system based on first interventional device position information of an interventional device within a patient obtained from a first image data indicative of a first location of the interventional device and obtained from a position sensor that is located on the interventional device within the patient at the first interventional device location,
   wherein the registration component updates the first registration by performing a second registration based on the first image data and a second interventional device position information of the interventional device within the patient obtained from intermediate image data indicative of a second location of the interventional device and obtained from the position sensor located at the second interventional device location, wherein the intermediate image data is acquired by an imaging device after the interventional device is moved to the second location; and
   a presentation component for presenting the intermediate image data and the interventional device position information.

2. The system of claim 1, wherein the position sensor is selected from the group consisting of an electromagnetic sensor, a magnetic sensor, an optical sensor, and an ultrasonic sensor.

3. The system of claim 1, wherein the position sensor is positioned near an end of the interventional device that is within the patient.

4. The system of claim 1, wherein the position sensor is localized in the intermediate image data.

5. The system of claim 1, wherein the first registration registers the image space coordinate system and the interventional space coordinate system via a first set of spatial coordinates of at least three fiducial markers identified within image data and a second set of spatial coordinates of the at least three fiducial markers spatially identified on the patient by inducing an electromagnetic field about the at least three fiducial markers and identifying each marker by touching the marker with a probe.

6. The system of claim 5, further including a transformation component that generates a mapping between coordinates in the coordinate systems.

7. The system of claim 1, wherein the registration component updates a previous registration after each of a plurality of successive incremental advances of the interventional device within the patient.

8. The system of claim 5, wherein the registration component uses interventional device position information corresponding to at least two of the plurality of successive incremental advances and fiducial marker information of the at least three fiducial markers to update a previous registration.

9. The system of claim 8, wherein the interventional device position information is weighted as a function of acquisition time.

10. The system of claim 1, wherein the interventional device is one of a needle, a catheter, and a guide wire.

11. The system of claim 1, further including a computer tomography scanner that generates the image data.

12. A system, comprising:
    a first component that performs a first registration of an image space coordinate system and an interventional space coordinate system based on a spatial location of at least three fiducial markers identified within first image data and spatial coordinates of the at least three fiducial markers spatially identified on a patient with a position measurement device; and
    a second component that updates the first registration by performing a second registration using the first image data and interventional device position information obtained from an intermediate image generated from image data acquired after the interventional device is advanced into the patient to update a position measurement performed by the position measurement device.

13. The system of claim 12, wherein the position information provided by a calibrated position measurement device locates the interventional device before each advance.

14. The system of claim 12, wherein the position measurement device is calibrated after each advance of the interventional device with corresponding position information acquired after each incremental advance.

15. The system of claim 12, wherein the calibration adjusts the position measurement device to correct for inaccuracies of the position measurement device.

16. The system of claim 12, wherein the sensor is a coil that senses an electromagnetic field.

17. The system of claim 12, wherein the interventional device includes a minimally invasive surgical tool having an electromagnetic sensor.

18. The system of claim 12, wherein the first component uses the interventional device position information obtained from the intermediate image and interventional device position information from a sensor coil on the interventional device along with the spatial location of at least three fiducial markers to update the registration.

19. A method, comprising:
    performing a first registration of an image space coordinate system with an interventional system coordinate system based on fiducial marker position information for a plurality of fiducial markers to obtain first image data including the fiducial marker position information; and
    updating the first registration by using the first image data and performing a second registration based on interventional device position information obtained from an intermediate image, interventional device position information obtained from an electromagnetic sensor located on the interventional device, and a spatial location of the at least three fiducial markers, wherein the interventional device position information obtained from the intermediate image and the electromagnetic sensor is acquired after advancing the interventional device along a path within the patient.

20. The method of claim 19, wherein the electromagnetic sensor is located at a distal end of the interventional device.

21. The method of claim 19, further including calibrating the position measurement device with the interventional device position information obtained from the intermediate image.

22. The method of claim 19, further including localizing three fiducial markers placed on the skin of a patient about a region of interest in a generally non-collinear orientation.

23. The method of claim 19, further including performing at least one subsequent registration update after a second advance of the interventional device along the planned path.

24. The method of claim 19, further including updating the first registration using interventional device position information corresponding to at least two of a plurality of successive incremental advances and the fiducial marker information to update the first registration.

25. The method of claim 19, further including acquiring further fiducial marker position information along with the interventional device position information and using the newly acquired further fiducial marker position information and the interventional device position information to update the first registration.

26. A non-transitory computer readable storage medium containing instructions which, when executed by a computer, cause the computer to carry out the method of claim 19.

27. A system, comprising:
- means for performing a first registration of an image space coordinate system with an interventional system coordinate system based on fiducial marker position information for a plurality of fiducial markers to obtain first image data including the fiducial marker position information; and
- means for updating the first registration by using the first image data and performing a second registration based on interventional device position information obtained from an intermediate image and interventional device position information obtained from an electromagnetic sensor on the interventional device and a spatial location of the plurality of fiducial markers, wherein the interventional device position information obtained from the intermediate image and the electromagnetic sensor is acquired after advancing the interventional device along a path within the patient.

* * * * *